United States Patent [19]

Gruneisen

[11] Patent Number: 5,129,103

[45] Date of Patent: Jul. 14, 1992

[54] VISORED CAP AND FLEXIBLE BLANK THEREFOR

[76] Inventor: Albert Gruneisen, 1800 Spring Dr., Louisville, Ky. 40205

[21] Appl. No.: 606,908

[22] Filed: Oct. 31, 1990

Related U.S. Application Data

[63] Continuation-in-part of Ser. No. 329,295, Mar. 27, 1989, Pat. No. 4,969,213.

[51] Int. Cl.⁵ ............................................... A61F 9/00
[52] U.S. Cl. ........................................... 2/12; 2/171; 2/195; 2/200
[58] Field of Search ............... 2/12, 171, 171.1, 171.2, 2/172, 173, 173.5, 175, 177, 195, 196, 200, 206, 209.1, 209.3, 209.7, 15

[56] References Cited

U.S. PATENT DOCUMENTS

| | | | |
|---|---|---|---|
| 727,173 | 5/1903 | Merrell | 2/206 |
| 766,419 | 8/1904 | Breck | 2/195 |
| 1,401,758 | 12/1921 | Carleton | 2/12 |
| 1,999,252 | 4/1935 | Mullendore | 2/171 |
| 2,019,028 | 10/1935 | Sternberg | 2/171 |
| 2,092,805 | 9/1937 | Jones | 2/12 |
| 2,293,436 | 8/1942 | Kelley | 2/12 |
| 2,545,097 | 3/1951 | Lucas | 2/12 |
| 2,594,906 | 4/1952 | Gardner | 2/200 |
| 2,787,791 | 4/1957 | Linney | 2/12 |
| 2,795,796 | 6/1957 | Ray | 2/206 |
| 2,964,757 | 12/1960 | Jarvis | 2/173 |
| 2,988,743 | 6/1961 | Wagenfeld | 2/12 |
| 3,041,628 | 7/1962 | Fisk | 2/195 |
| 3,082,429 | 3/1963 | DeVillers | 2/195 |
| 3,184,575 | 5/1965 | Pennington | 2/12 |
| 4,027,340 | 6/1977 | Hadtke | 2/206 |
| 4,121,304 | 10/1978 | Cooper | 2/206 |
| 4,246,659 | 1/1981 | Lyons | 2/209.3 |
| 4,247,957 | 2/1981 | Rogers | 2/12 |
| 4,262,367 | 4/1981 | Herrin | 2/12 |
| 4,386,126 | 5/1983 | Turner | 2/12 |
| 4,468,818 | 9/1984 | Flannery | 2/195 |
| 4,670,910 | 6/1987 | Rosasco | 2/195 |
| 4,747,164 | 5/1988 | Foulke | 2/171 |
| 4,852,186 | 8/1989 | Landis | 2/196 |
| 4,969,213 | 11/1990 | Gruneisen | 2/171 |

FOREIGN PATENT DOCUMENTS

| | | | |
|---|---|---|---|
| 1129660 | 1/1957 | France | 2/12 |
| 873083 | 7/1961 | United Kingdom | 2/200 |

Primary Examiner—Werner H. Schroeder
Assistant Examiner—Diana L. Biefeld
Attorney, Agent, or Firm—Jon C. Winger

[57] ABSTRACT

A disposable visored cap to be worn during outdoor or indoor activities to shade the wearer's eyes from the light, or as a cap representing a club mascot or displaying advertisements. The visored cap, and blank therefor, is fabricated of a flexible material such as paper, cardboard, and the like. The blank has a first end edge, a second end edge, an arcuate fold line spaced from the first end edge defining a visor therebetween, and defining a front panel between the arcuate fold line and second end edge. To fold the blank to form the cap, the visor is folded in a downwardly direction about the arcuate fold line to project outwardly from the front panel and the front panel depends from the arcuate fold line.

6 Claims, 3 Drawing Sheets

VISORED CAP AND FLEXIBLE BLANK THEREFOR

CROSS-REFERENCE TO RELATED APPLICATION

This is a Continuation-in-Part of application Ser. No. No. 07/329,295, Filed Mar. 27, 1989, now U.S. Pat. No. 4,969,213.

BACKGROUND OF THE INVENTION

The invention relates to visored caps and the like, such as masks, and a blank for forming the cap of a single sheet of flexible material.

An object of the present invention is to provide a visored cap and the like, and blank therefor which is inexpensive to make and, therefore, is disposable even after one use. Thusly, the visored cap or mask can be distributed for free, or sold at a minimum cost to the purchaser which makes it ideal for advertisers to promote their product or service, or promote a sporting event, or to fans attending a sporting event to show their team loyalty.

Visor caps made of a blank of flexible sheet material are, per se, known. Various examples of such caps and blanks are shown in U.S. Pat. No. 1,401,758 issued on Dec. 27, 1921 to W. A. Carleton, U.S. Pat. No. 2,092,805 issued on Sep. 14, 1937 to J. P. Jones, U.S. Pat. No. 2,293,436 issued on Aug. 18, 1942 to J. M. Kelley, U.S. Pat. No. 2,545,097 issued on Mar. 13, 1951 to G. R. Lucas, U.S. Pat. No. 2,787,791 issued on Apr. 9, 1957 to A. T. Linney, U.S. Pat. No. 2,988,743 issued on Jun. 30, 1961 to G. B. Wagenfeld, U.S. Pat. No. 4,262,367 issued on Apr. 21, 1981 to Lenny Herrin, and U.S. Pat. No. 4,670,910 issued on Jun. 9, 1987 to Leroy Rosasco.

SUMMARY OF THE INVENTION

In one embodiment, the present invention provides a flexible blank for a visored cap comprising a first end edge; a second end edge opposite the first edge; the bisecting centerline of the first end edge being in alignment with the bisecting centerline of the second end edge, and each of the terminate ends of the first end edge being in alignment with a different one of the terminate ends of the second end edge; first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge; an arcuate fold line extending between the first and second side edges convexly facing the first end edge with the bisecting centerline of the arcuate fold line in alignment with the bisecting centerline of the first end edge; and the bisecting centerline of the arcuate fold line being in alignment with the bisecting centerlines of the first arcuate end edge, the second end edge.

In another embodiment, the present invention provides a visored cap to be worn on a person's head comprising a continuous flexible blank having a first end edge, a second end edge opposite the first end edge wherein the bisecting centerline of the first end edge is in alignment with the bisecting centerline of the second end edge, and each of the terminating ends of the first end edge being in alignment with a different one of the terminal ends of the second end edge, first and second side edges, the first side edge interconnecting one of the terminal ends of the first end edge and aligned one of the terminal ends of the second end edge, and the second side edge interconnecting the other one of the terminal ends of the first end edge and the aligned other one of the terminal ends of the second end edge, an arcuate fold line extending between the first and second side edges convexly facing the first end edge with the bisecting centerline of the arcuate fold line in alignment with the bisecting centerline of the first end edge, the arcuate fold line and first end edge cooperating to define a visor portion between the arcuate fold line and the first end edge, and the arcuate fold line, and the arcuate fold line and second end edge cooperating to define a front panel portion, the visor portion is folded downwardly about the arcuate fold line to form a curved visor projecting outwardly from the outside surface of the front panel and the front panel depending from the arcuate fold line.

BRIEF DESCRIPTION OF THE DRAWINGS

A better understanding of the invention will be had upon reference to the following description in conjunction with the appended drawings wherein like numerals refer to like parts throughout the several views and in which.

DETAILED DESCRIPTION OF THE EMBODIMENTS

Figure 1:
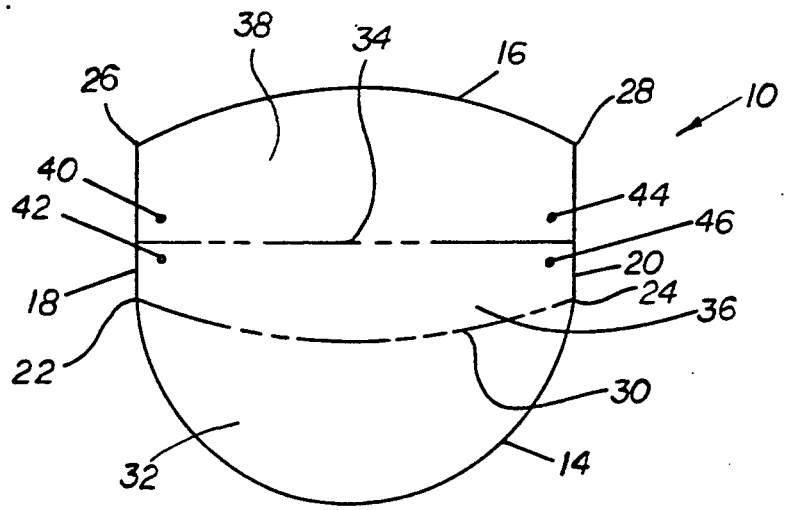
FIG. 1 is a plan view of one embodiment of a novel blank of the invention from which a visored cap of the present invention is formed.
Figure 2:
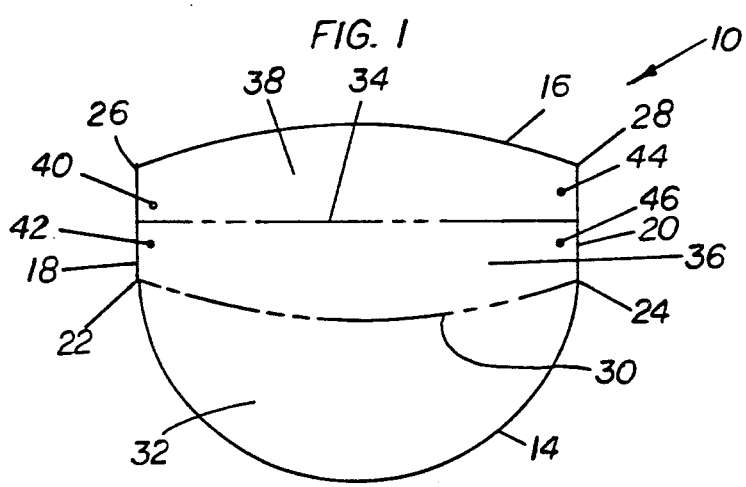
FIG. 2 is a plan view of another embodiment of a novel blank of the invention.
Figure 4:
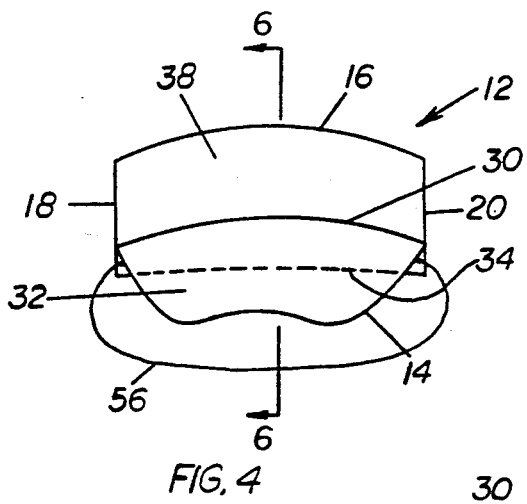
FIG. 4 is a front view of a visored cap of the present invention.
Figure 5:
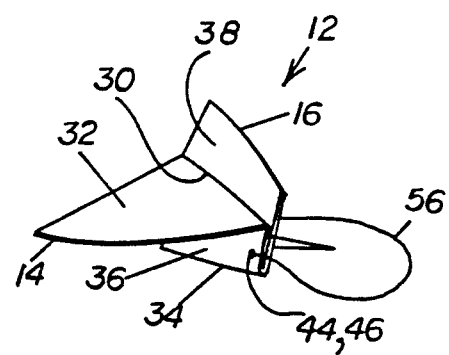
FIG. 5 is a side view of the visored cap of FIG. 4.
Figure 6:
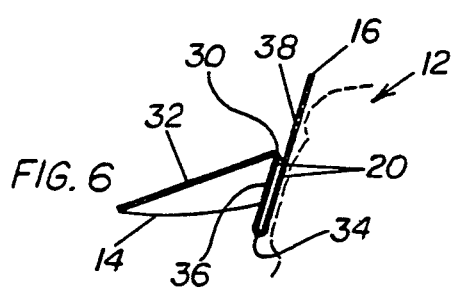
FIG. 6 is a cross-sectional side view as seen in the direction of arrows 6—6 in FIG. 4.

With reference to FIGS. 1 and 2, there is a flexible blank, generally denoted as the numeral 10, for forming a visor cap 12 (see FIGS. 4–6). The blank 10 is a sheet of flexible material such as paper, cardboard, plastic and the like. The blank 10 comprises a first end edge 14, a second end edge 16 opposite the first end edge 14, a first side edge 18, and a second side edge 20. As shown in FIGS. 1 and 2, the first end edge 14 is a convex arcuate edge and the second end edge 16 is also a convex arcuate edge. The first and second arcuate end edges 14 and 16 concavely face each other, an imaginary bisecting centerline of the first end edge 14 is in alignment with the bisecting centerline of the second end edge 16, and the terminal ends 22, 24 of the first end edge 14 are each in alignment with a different one of the terminating ends 26, 28 of the second end edge 16. The first side edge 18 interconnects one of the terminal ends 22 of the first end edge 14 and one of the aligned one of the terminal ends 26 of the second end edge 16. The second side edge 20 interconnects the other one of the terminal ends 24 of the first end edge 14 and the aligned other one of the terminal ends 28 of the second end edge 16. As shown, the first and second side edges 18 and 20 are straight edges, parallel to each other and parallel to the aligned imaginary bisecting centerlines of the first and second end edges 14, 16. An arcuate fold line 30 extends between the first and second side edges 18, 20 convexly facing the first end edge 14 with an imaginary bisecting centerline of the arcuate fold line 30 in alignment with the imaginary bisecting centerline of the first end edge 14 and the imaginary bisecting centerline of the second end edge 16. The space between the arcuate fold line 30 and the first end edge 14 defines a visor 32 of the cap 12. A straight fold line 34 is located between the second end edge 16 and the arcuate fold line 30 extending between the first and second side edges 18, 20 with an imaginary bisecting centerline of the straight fold line 34 in alignment with the bisecting centerlines of the first arcuate end edge 14, the second end edge 16, and the arcuate fold line 30. The space between the arcuate fold line 30 and straight fold line 34 defines an intermediate portion 36 of the cap 12, and the space between the straight fold line 34 and the second end edge 16 defines a front panel 38 of the cap 12. As shown in FIGS. 1 and 2, the intersections of the arcuate fold line 30 and the first side edge 18 coincides with the intersection of one of the terminal ends 22 of the first end edge 14 and the first side edge 18. Similarly, the intersection of the arcuate fold line 30 and the second side edge 20 coincides with the intersection of the other one of the terminal ends 24 of the first end edge 14 and the second side edge 20.

With continued reference to FIGS. 1 and 2, a first pair of apertures 40, 42 and a second pair of apertures 44, 46 are formed through the blank 10. The first pair of apertures 40, 42 are located proximate the first side edge 18 with the aperture 40 being spaced to one side of the straight fold line 34 and the aperture 42 being spaced to the opposite side of the straight fold line 34. The other pair of apertures 44, 46 are located proximate the second side edge 20 with the aperture 44 being spaced to one side of the straight fold line 34 and the aperture 46 being spaced to the opposite side of the straight fold line 34. A centerline extending between one of the apertures 40 of the first pair and one of the apertures 44 of the second pair on one side of the straight fold line 34 is parallel to the straight fold line 34 and a centerline extending between the other one of the apertures 42 of the first pair and the other one of the apertures 46 of the second pair on the other side of the straight fold line 34 is parallel to the straight fold line 34.

Comparing FIGS. 1 and 2, essentially the only difference therebetween are dimensional. In the embodiment of FIG. 1, the intersections of the terminal ends 26, 28 of the second end edge 16 with the first and second side edges 18, 20, respectively, are spaced a greater distance from the straight fold line 34 than the distance by which the intersections of the terminal ends 22, 24 of the first end edge 14 with the first and second side edges 18, 20, respectively, are spaced from the straight fold line 34. By contrast, in the embodiment of FIG. 2, the intersections of the terminal ends 26, 28 of the second end edge 16 with the first and second side edges 18, 20, respectively, are spaced from the straight fold line 34 by a distance equal to the distance by which the intersections of the first end edge 14 with the first and second side edges 18, 20 are spaced from the straight fold line 34.

Figure 3:
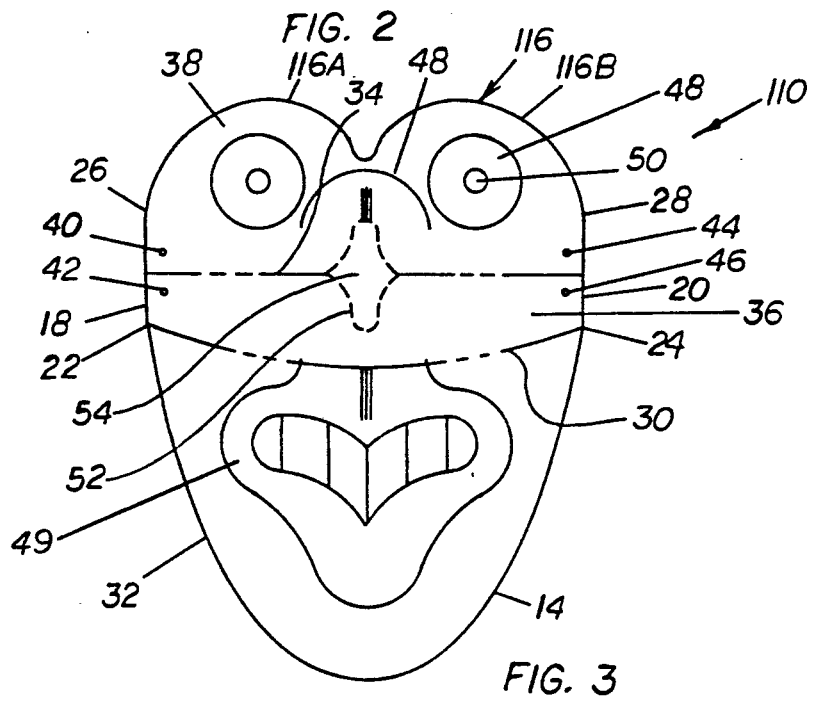
FIG. 3 is a plan view of yet another embodiment of a novel blank of the invention.
Figure 7:
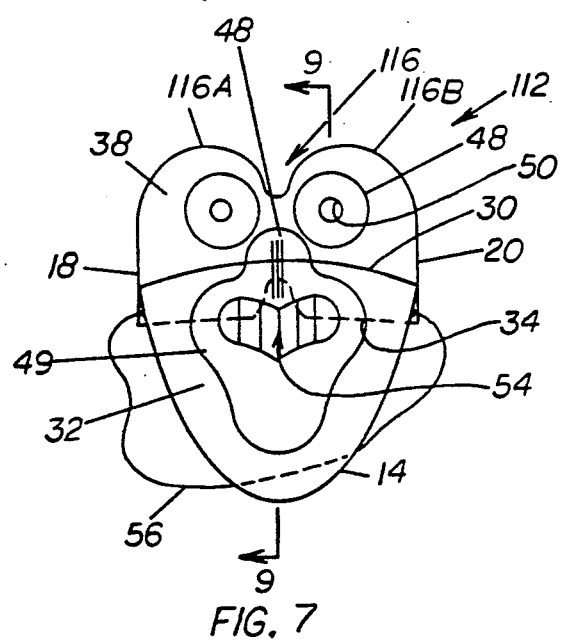
FIG. 7 is a front view of a visor cap formed of the blank of FIG. 3.
Figure 8:
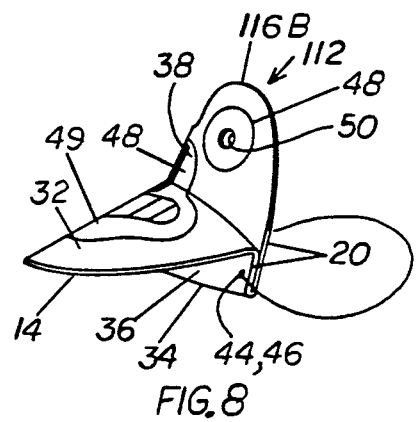
FIG. 8 is a cross-sectional side view as seen in the direction of arrows 8—8 in FIG. 7.

Now with reference to FIG. 3, there is shown another embodiment of a cap blank, generally denoted as the numeral 110, which is similar in most respects to the cap blank 10 of FIGS. 1 and 2. Therefore, for the sake of brevity, similar elements between the cap blank 110 and cap blank 10 are denoted by identical numerals in FIG. 3 and a description thereof will not be repeated. The cap blank 110 differs from the cap blank 10 mainly in peripheral configuration. In the cap blank 110, the second end edge 116 is configured with two arcuate portions 116A, 116B which are equally spaced to opposite lateral sides of the imaginary bisecting centerline of the second end edge 116. Thus, at least a portion of the second end edge 116 is spaced a greater distance from the straight fold line 34 than the distance by which any portion of the arcuate fold line 30 is spaced from the straight fold line 34. The cap blank 110 includes indicia 48 on the front panel 38 and different indicia 49 on the visor 32. The indicia 48 and indicia 49 cooperate or mate when the cap blank 110 is folded to form a cap/mask 112 (see FIGS. 7 and 8) to form a complete unitary design. Toward this objective, the indicia 49 terminates at about the arcuate fold line 30 and the indicia 48 terminates at a distance from the straight fold line 34 about equal to the distance between the arcuate fold line 30 and straight fold line 34. As can be best seen in FIGS. 7 and 8, the termination of the indicia 49 mates in alignment with the termination of the indicia 48 such that the indicia 48 and indicia 49 cooperate at the arcuate fold line 30 when the blank 110 is folded to form the cap/mask 112 to form the complete unitary design. This configuration can be used in the application wherein the invention can be worn as a cap (see FIG. 6) or mask 112 (see FIG. 9) and can represent, for example, a sports team mascot or the like. In this event, indicia 48 printed on the mask/cap front panel 38 represents eyes and a portion of a nose or bill of a mascot, and the indicia 49 printed on the visor portion 132 can be decorated to represent the other portion of the nose, or bill of the mascot. For example, the mascot for the University of Louisville in Louisville, KY is a cardinal bird. In this case, the cap/visor 112 can be decorated to resemble the head of a cardinal with the indicia 48 on the front panel representing the eyes and upper portion of the bird's bill and the indicia 49 on the visor portion 132 representing the lower or remaining portion of the bird's bill. Advantageously, the blank 110 is formed to be selectively worn as a mask by including closely spaced perforations 52 formed through the blank 110 defining a parallelogram 54 shaped area with two of the opposite corners of the parallelogram on the straight fold line 34 and the other two of the opposite corners of the parallelogram on an imaginary bisecting centerline of the straight fold line 34 and spaced to opposite lateral sides of the straight fold line 34. In addition, appropriate holes 50 can be formed through the front panel 38 to allow the person wearing the mask to see. As will hereinafter become more clear in reference to the discussion of FIGS. 7 and 8, the material of the parallelogram shaped area 54 will be removed to provide a clearance for the bridge of a wearer's nose in the event the cap/mask 110 is worn as a mask over the wearer's face.

With reference now to FIGS. 4, 5, and 6, there is shown the cap 12. To form the cap 12 from the blank 10, the intermediate portion 36 of the blank 10 is folded upwardly about the straight fold line 34 to overlay the exterior surface of the front panel portion 38 of the blank 10, and the visor portion 32 is folded in the opposite direction or downwardly about the arcuate fold line 30 to project outwardly away from the outside or exterior surface of the front panel portion 38. When this is done, the aperture 40 of the first aperture pair is in registration with the other aperture 42 of the first aperture pair, and the aperture 44 of the second aperture pair is in registration with the other aperture 46 of the second aperture pair. When the visor portion 32 is folded downwardly about the arcuate fold line 30, the intermediate portion 36 and front panel portion 38 are formed into a curve corresponding to the curvature of the arcuate fold line 30 such that the intermediate portion 36 is on the concave exterior side of the front panel portion 38. An elastic headband 56 is affixed to the cap 10 by threading one end through the registered aperture 40, 42 of the first aperture pair and by threading the other end through the registered apertures 44, 46 of the second aperture pair. The opposite ends of the elastic headband 56 are then secured in place so as not to pull out of the apertures by various means such as a fastener (not shown) or a knot (not shown). When the cap is placed on the wearer's head, the concave side of the front panel 38 is the headband and is placed against the wearer's forehead with the visor projecting outwardly above the wearer's eyes and the elastic headband 56 encompassing the wearer's head to hold the cap 12 in place.

Figure 9:
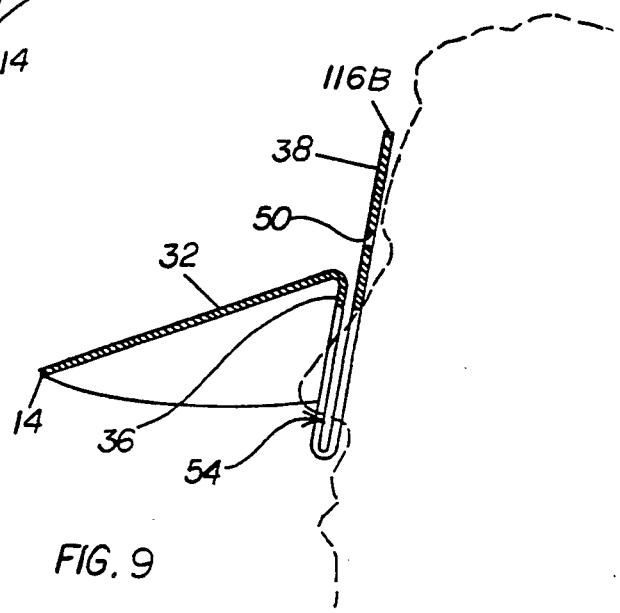
FIG. 9 is a cross-sectional side view of the cap of FIG. 8 worn as a mask.

With reference to FIG. 9, there is shown the cap 112 worn as a mask. To form the mask 112 from the blank 110, the intermediate portion 36 of the blank 110 is folded upwardly about the straight fold line 34 to overlay the exterior surface of the front panel portion 38 of the blank 110 and the visor portion 32 is folded in the opposite direction or downwardly about the arcuate fold line 30 to project outwardly from the outside or exterior surface of the front panel portion 38, and the elastic headband 56 is attached to the mask 112 as discussed above in regard to the cap 12. The parallelogram shaped area 54 defined by the perforations 52 is punched out or removed to form a clearance notch in the center of the intermediate portion 36 and front panel portion 38 beneath the visor portion 32 and centered on the imaginary bisecting centerline of the visor portion 32 for receiving the bridge of the wearer's nose. When the mask 112 is placed on the wearer's head, the concave side of the front panel 38 beneath the visor portion 32 will be against the wearer's cheekbones below the eyes, with the visor portion 32 projecting outwardly below the wearer's eyes, and the front panel portion 38 extending upwardly in front of the wearer's eyes. The mask 112 can, of course, also be worn as a visored cap by merely positioning it such that concave interior side of the front panel portion 38 is against the wearer's forehead. The elastic headband 56 encompasses the wearer's head to hold the mask/cap 112 in place.

Figure 10:
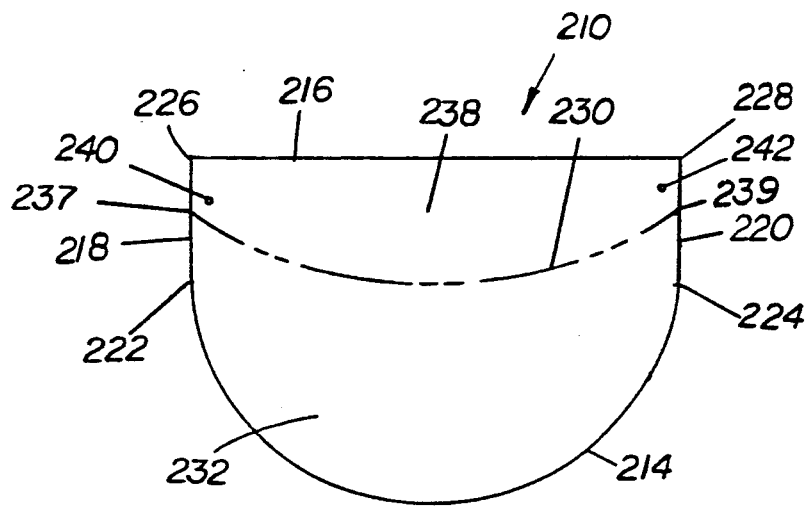
FIG. 10 is a plan view of yet another embodiment of a novel blank of the invention from which a visored cap of the present invention is formed.
Figure 11:
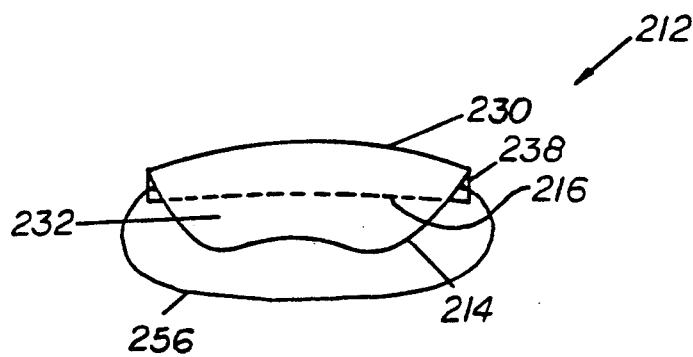
FIG. 11 is a front view of a visored cap of the invention formed from the blank of FIG. 10; and, FIG. 12 is a side view of the visored cap of FIG. 11.
Figure 12:
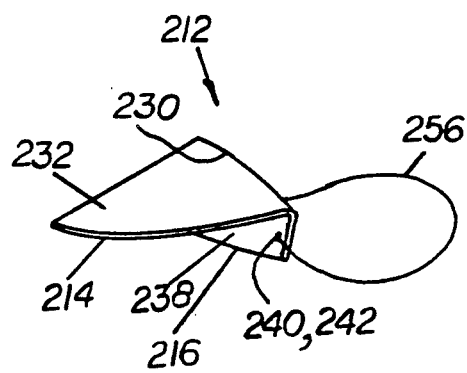

With reference to FIG. 10, there is shown a flexible blank 210, for forming a visor cap 212 (see FIGS. 11 and 12). The blank 210 is a sheet of flexible material such as paper, cardboard, plastic and the like. The blank 210 comprises a first end edge 214, a second end edge 216 opposite the first end edge 214, a first side edge 218, and a second side edge 220. As shown in FIG. 10, the first end edge 214 is a convex arcuate edge and the second end edge 216 continuous or uninterrupted is a straight edge. The first arcuate end edge 214 concavely faces the straight second end edge 216. An imaginary bisecting centerline of the first end edge 214 is in alignment with an imaginary bisecting centerline of the second end edge 216, and the terminating ends 222, 224 of the first end edge 214 are each in alignment with a different one of the terminating ends 226, 228 of the second end edge 216. The first side edge 218 interconnects one of the terminal ends 222 of the first end edge 214 and one of the aligned one of the terminal ends 226 of the second end edge 216. The second side edge 220 interconnects the other one of the terminal ends 224 of the first end edge 214 and the aligned other one of the terminal ends 228 of the second end edge 216. As shown, the first and second side edges 218 and 220 are straight edges, parallel to each other and parallel to the aligned imaginary bisecting centerlines of the first and second end edges 214, 216. An arcuate fold line 230 extends between the first and second side edges 218, 220 convexly facing the first end edge 214 with an imaginary bisecting centerline of the arcuate fold line 230 in alignment with the imaginary bisecting centerline of the first end edge 214 and the imaginary bisecting centerline of the second end edge 216. The space between the arcuate fold line 230 and the first end edge 214 define a visor 232 of the cap 212, and the space between the arcuate fold line 230 and second end edge 216 defines a front panel 238 of the cap 212. As shown in FIG. 10, the terminating end 237 of the arcuate fold line 230 intersects the first side edge 218 between the terminal end 222 of the first end edge 214 and the terminal end 226 of the second end edge 216, and the terminating end 239 of the arcuate fold line 230 intersects the second side edge 220 between the terminal end 224 of the first end edge 214 and the terminal end 228 of the second end edge 216. Prferably, and as shown in FIG. 10, the terminal end 237 of the arcuate fold line 230 is closer to the terminal end 226 of the second end edge 216 than to the terminal end 222 of the first end edge 214, and the terminal end 239 of the arcuate fold line 230 is closer to the terminal end 228 of the second end edge 216 than to the terminal end 224 of the first end edge 214.

With continued reference to FIG. 10, a first aperture 240 and a second aperture 242 are formed through the blank 210. The first aperture 240 is located proximate the first side edge 218 midway between the terminal end 226 of the second end edge 216 and the terminal end 237 of the arcuate fold line 230, and the second aperture 242 is located proximate the second side edge 220 midway between the terminal end 228 of the second end edge 216 and the terminal end 239 of the arcuate fold line 230. An imaginary centerline extending between the first aperture 240 and second aperture 242 is parallel to an imaginary straight line extending between the terminal ends 222, 224 of the first end edge 214.

Now with reference to FIGS. 11 and 12, there is shown the cap 212 having an elastic band 256 attached for holding the cap on a wearer's head. To form the cap 212 from the blank 210, the visor portion 232 is folded downwardly about the arcuate fold line 230 such that the front panel 238 depends from the arcuate fold line 230 and the visor panel 232 projects outwardly from the outside or exterior surface of the front panel portion 238. When the visor portion 232 is folded downwardly about the arcuate fold line 230, the front panel portion 238 is formed into a curve corresponding to the curvature of the arcuate fold line 230 such that the depending front panel portion 238 convexly faces toward the visor portion 232. The elastic headband 256 is attached at one of its ends through the first aperture 240 and at its other end through the second aperture 242 in the front panel 238. When the cap 212 is placed on a wearer's head, the concave side of the front panel portion 238 is the headband of the cap and is placed against the wearer's forehead with the visor 232 projecting outwardly above the wearer's eyes and the elastic headband 256 encompassing the wearer's head to hold the cap 212 in place.

The foregoing detailed description is given primarily for clearness of understanding and no unnecessary limitations are to be understood therefrom for modifications will become obvious to those skilled in the art and may be made without departing from the spirit of the invention and scope of the appended claims.

I claim:

1. A flexible blank for a visored cap comprising:
   a first end edge having two terminal ends;
   a second uninterrupted end edge opposite the first end edge, the second end edge having two terminal ends;
   an imaginary bisecting centerline of the first end edge being in alignment with an imaginary bisecting centerline of the second end edge, and each of the terminal ends of the first end edge being in alignment with a different one of the terminal ends of the second end edge;
   first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge; and
   an arcuate fold line having two terminal ends extending between the first and second side edges convexly facing the first end edge with an imaginary bisecting centerline of the arcuate fold line in alignment with the imaginary bisecting centerline of the first end edge, one terminal end of the arcuate fold line intersecting the first side edge between the terminal ends of the first end edge and second end edge, and the other terminal end of the arcuate fold line intersecting the second side edge between the terminal ends of the first end edge and second end edge, the area between the arcuate fold line and first end edge defining a visor portion of the visored cap and the area between the arcuate fold line and second end edge defining a front panel portion of the visored cap.

2. The flexible blank of claim 1, wherein the intersections of the terminal ends of the arcuate fold line with the first and second side edges are spaced a smaller distance from the intersections of the terminal ends of the second end edge with the first and second side edges than from the intersections of the terminal ends of the first end edge with the first and second side edges.

3. The flexible blank of claim 1, wherein the first end edge is an arcuate edge in concave aligned facing relationship with second end edge.

4. The flexible blank of claim 1, wherein the first and second side edges are parallel straight edges and are parallel to the imaginary bisecting centerlines of the first end edge and second end edge.

5. The flexible blank of claim 1, further comprising:
   a first aperture formed through the panel portion of the blank proximate the first side edge midway between the terminal end of the second end edge and the terminal end of the arcuate fold line;
   a second aperture formed through the panel portion of the blank proximate the second side edge midway between the terminal end of the second end edge and the terminal end of the arcuate fold line, an imaginary centerline extending between the apertures being parallel to an imaginary straight line extending between the terminal ends of the first end edge.

6. A visored cap to be worn on a person's head comprising a continuous flexible blank having a first end edge and having two terminal ends, a second uninterrupted end edge opposite the first end edge, the second end edge having two terminal ends, wherein an imaginary bisecting centerline of the first end edge is in alignment with an imaginary bisecting centerline of the second end edge, and each of the terminal ends of the first end edge being in alignment with a different one of the terminal ends of the second end edge, first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge, an arcuate fold line having two terminal ends extending between the first and second side edges convexly facing the first end edge with an imaginary bisecting centerline of the arcuate fold line in alignment with the imaginary bisecting centerline of the first end edge, the arcuate fold line and first end edge cooperating to define a visor portion of cap between the arcuate fold line and the first end edge, the arcuate fold line and second end edge cooperating to define a front panel portion of the cap wherein the visor portion is folded downwardly about the arcuate fold line to form a curved visor projecting outwardly from the outside surface of the front panel and the front panel depends from the arcuate fold line to form a curved unitary uninterrupted front panel.

* * * * *